(12) United States Patent
Dussauze et al.

(10) Patent No.: US 7,517,698 B2
(45) Date of Patent: Apr. 14, 2009

(54) INSTALLATION AND PROCESS FOR AUTOMATIC PREPARATION OF SAMPLES

(75) Inventors: Jacques Dussauze, Plougastel-Daoulas (FR); Roger Delmas, Plougastel-Daoulas (FR); Goulven Cavalin, Brest (FR); Bernard-Jacky Munoz, Orvault (FR)

(73) Assignee: Hocer, Orvault (FR)

( * ) Notice: Subject to any disclaimer, the term of this patent is extended or adjusted under 35 U.S.C. 154(b) by 868 days.

(21) Appl. No.: 10/296,170

(22) PCT Filed: May 23, 2001

(86) PCT No.: PCT/FR01/01587

§ 371 (c)(1),
(2), (4) Date: Aug. 28, 2003

(87) PCT Pub. No.: WO01/90722

PCT Pub. Date: Nov. 29, 2001

(65) Prior Publication Data

US 2004/0038384 A1    Feb. 26, 2004

(30) Foreign Application Priority Data

May 23, 2000   (FR)   .................................... 00 06551

(51) Int. Cl.
*G01N 1/18*   (2006.01)

(52) U.S. Cl. ........................ 436/178; 436/180; 436/140; 422/70; 422/99

(58) Field of Classification Search .................... 422/70, 422/99–101; 436/180, 140, 178
See application file for complete search history.

(56) References Cited

U.S. PATENT DOCUMENTS

| 4,070,284 A | 1/1978 | Fujita et al. |
| 4,154,583 A | 5/1979 | Favre et al. |
| 4,500,432 A | 2/1985 | Poole et al. |
| 5,117,109 A | 5/1992 | Asakawa et al. |
| 5,449,902 A | 9/1995 | Yoshimura et al. |
| 5,512,168 A | 4/1996 | Fetner et al. |
| 5,630,943 A * | 5/1997 | Grill .......................... 210/659 |

FOREIGN PATENT DOCUMENTS

| EP | 0 571 716 | 12/1993 |
| EP | 0 892 267 | 1/1999 |
| WO | WO 93/07168 | 4/1993 |
| WO | WO 99/65587 | 12/1999 |

* cited by examiner

*Primary Examiner*—Jill Warden
*Assistant Examiner*—Jyoti Nagpaul
(74) *Attorney, Agent, or Firm*—Young & Thompson

(57) ABSTRACT

An installation for the automatic preparation of specimens by liquid/solid extraction on a column is characterized in that the extraction device comprises, on either side of the columns (3), a valve (4) controllable to switch one column (3) to the other to actuate one column (3) adapted to ensure the extraction function when another column (3) is in a non-operating condition, each switching valve (4) being connected to a controllable common direction reversing valve (5) arranged to impose one direction of circulation on the fluid in anyone of the columns (3) of the extraction device and to ensure its return to the valve (5) to distribute the treated fluid toward a circuit selectively either for its rejection or for its analysis.

14 Claims, 4 Drawing Sheets

INSTALLATION AND PROCESS FOR AUTOMATIC PREPARATION OF SAMPLES

Figure 1:
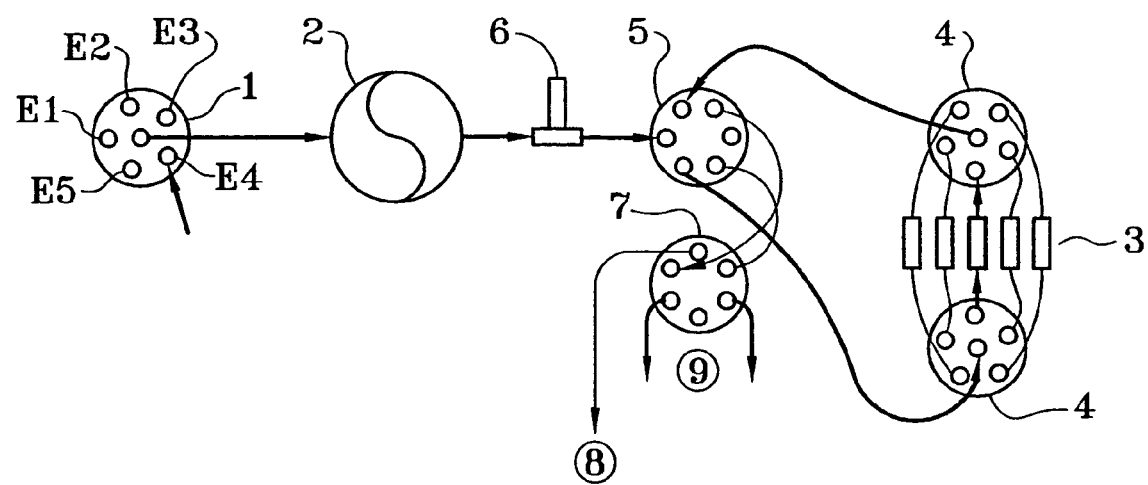

The present invention relates to an installation and a process for the automatic preparation of specimens for measurement by a suitable measuring system, such as a UV spectrometer, an infrared device, a fluorimeter, a mass spectrometer or the like.

The invention is applicable more particularly to following the process of natural or processed waters eventually adapted for consumption, adapted to contain pesticides or other organic pollutants. More and more severe rules concerning the permissible concentration thresholds in drinking water have required industry to develop new entirely automated installations permitting particularly a pre-concentration by liquid/solid extraction and a line analysis of the obtained concentrates. Certain installations thus developed have not met with the desired success because of the cost of the analyses. Such is the case with the system developed by the ZYMARCK company. This installation carries out a line concentration on an absorbent disk. A single measurement is carried out per disk. Once the measurement is carried out, the single use absorbent disk is discarded. As a result, there is a high cost of analysis. Similarly, the installation developed by the SPARK company is a concentration installation using a high cartridge. This installation permits the line elution in the direction of loading of a specimen. There is no reconditioning of the cartridge which is used but once. Moreover, the fact of working at high pressure gives rise to increased cost of the elements necessary for production of the installation. Other companies, such as the HEWLETT PACKARD company, have however envisaged the operation of a low pressure installation. In the case of this installation, there is provided a carousel carrying several low pressure cartridges. This carousel, serving as a cartridge carrier, connects each specimen to a new cartridge. The introduction of the specimen into the cartridge takes place by percolation. Elution and loading are carried out in the same direction. There again results a single use of the cartridge. The fact of having a cartridge carrier however permits the use in an autonomous manner of such an installation for a relatively long period of time. Finally, other documents such as U.S. Pat. Nos. 4,070,284, 4,500,432, EP 0 571 716, U.S. Pat. No. 5,449,902, WO 99/65587 and U.S. Pat. No. 5,117,109 illustrate the prior art of the invention.

An object of the present invention is to provide an installation and process for the automatic preparation of specimens whose respective designs permit on the one hand reducing the wear on the columns of the extraction device, thereby permitting their re-use for a large number of times under conditions of total repeatability, on the other hand to operate in a completely automatic and autonomous manner over a long period of time.

Another object of the present invention is to provide an installation and a process whose designs permit working at low pressure so as to reduce the cost of production and use of such an installation.

Another object of the present invention is to provide an installation whose flexibility of use permits perfect control of the liquid/solid extraction thanks to the possibility of programming and configuring as required the different steps of the extraction process.

To this end, the invention has for its object an installation for the automatic preparation of specimens, particularly for concentrates comprising organic materials dissolved in a liquid phase, for analysis on a suitable measuring system such as a UV spectrometer, an infrared device, a fluorimeter, a mass spectrometer or the like, this installation comprising a) a device for taking a liquid specimen,
b) a distribution device comprising a preferably low pressure valve capable of selecting either the specimen, or one of the different solvents or reagents needed for a liquid/solid extraction process,
c) a low pressure pump permitting supplying at the selected flow rate a liquid/solid extraction device,
d) a liquid/solid extraction device constituted by a plurality of columns each comprising at least one adsorbent phase, the installation being characterized in that the extraction device comprises, on each side of the column, a controllable valve for switching from one column to another to place in action a column adapted to ensure the extraction function when the other column is in a non-operating condition, each switching valve being connected to a common direction reversing valve interposed between the low pressure valve and the switching valves, this controllable direction reversing valve being arranged to impose a direction of circulation of the fluid in any one of the columns of the extraction device and to ensure its return to said valve to distribute the treated fluid toward a selective circuit either for rejection or for analysis.

Thanks to the design of the installation, which permits on the one hand automatic switching from one column to the other, on the other hand a regeneration of the column after each analysis thanks to a bi-directional circulation and at low pressure of the fluids in the column, it is possible to carry out more than 400 analyses in line without requiring the intervention of an operator and this according to a controlled work protocol.

The invention also has for its object a process for the preparation of fluid specimens, in particular concentrates, by liquid/solid extraction, for line analysis in a suitable measuring system such as a UV spectrometer, an infrared device, a fluorimeter, a spectrometer or the like, characterized in that it consists in taking a specimen, supplying at the selected flow rate a specimen or solvents to a column extraction device, causing to circulate by means of a direction reversing valve the specimen and/or the solvents either in one direction, or in the other in said extraction device, collecting at the inverting valve, no matter what the direction of circulation, the treated fluid to direct it toward a selector delivering the treated fluid either to an analysis device or toward a rejection installation, detecting in real time and continuously the condition of wear of the column (3) ensuring the extraction function and actuating, by means of switching valves (4), another column (3) adapted to ensure the extraction function when the active column (3) is detected as being in a non-functioning condition.

Such a process permits a reuse of each column so as to be able to carry out more than 80 analyses in line.

Figure 2:
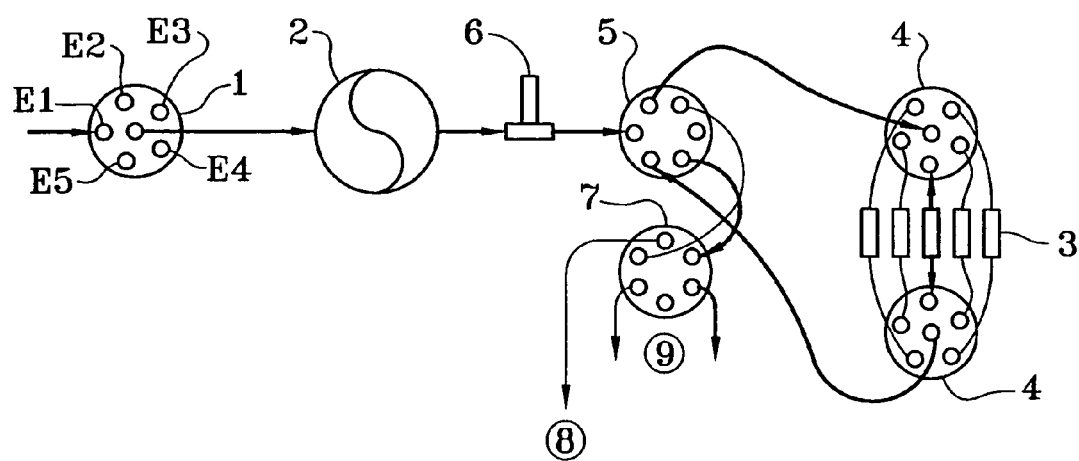
Figure 3:
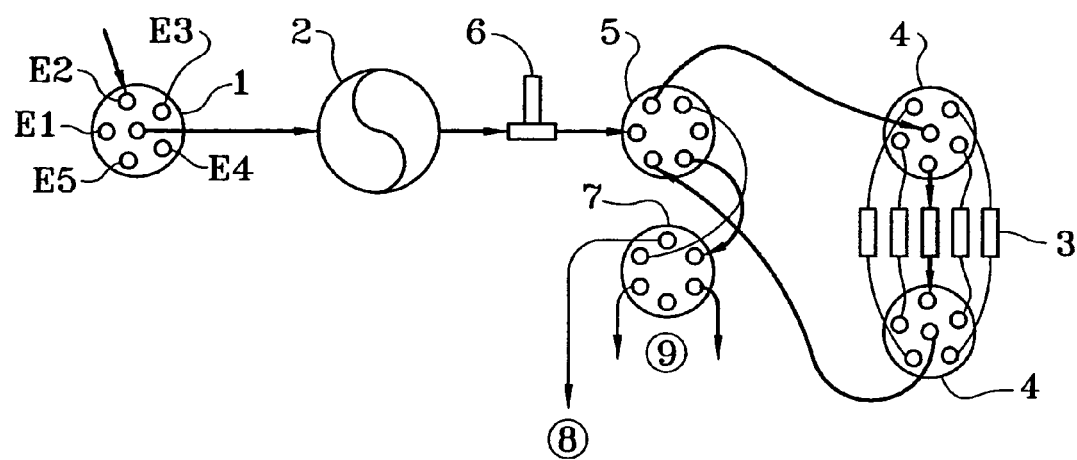
Figure 4:
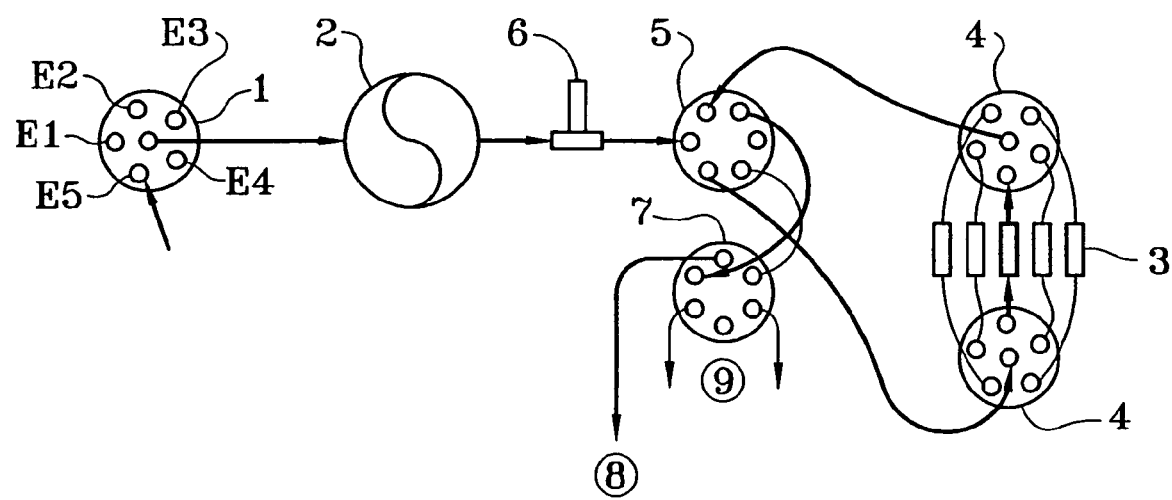

The invention will be better understood from a reading of the following description of embodiments, with reference to the accompanying drawings, in which:

FIGS. 1 to 4 represent schematically the different constituent elements of the installation and their respective positioning in the course of four cycles of an analysis including successively a regeneration cycle, a specimen loading cycle, a rinsing cycle and an elution cycle.

The installation for the automatic preparation of the specimens is more particularly adapted to permit the preparation of concentrates of organic compounds dissolved in a liquid phase. Such an installation is for example particularly adapted to the line analysis of specimens of natural or treated waters eventually destined for consumption, whose content in organic micro-pollutants, in particular in pesticides, must be controlled.

This installation comprises, in a manner known per se, a device for taking a liquid specimen to be analyzed, this taking device being adapted to be constituted by a simple pump (not shown). Downstream of this taking device, there is provided a distribution device comprising a valve 1, preferably low pressure, capable of selecting either the specimen, or one of the different solvents or reagents needed for the liquid/solid extraction process. In the illustrated examples, this low pressure valve 1 comprises several inlets $E_1$ to $E_5$, each connected to a solvent or to a reagent or to the specimen, and a common central outlet connecting the distribution device to a low pressure volumetric pump 2. It is to be noted that, by low pressure, there is meant a pressure below 7 bars. By way of example of a distribution device, there can be used a valve trademarked Rheodyne-Labpro valve, of the low pressure 7 passage and 6 position type.

The low pressure volumetric pump 2 itself permits supplying at the selected flow rate a liquid/solid extraction device constituted by a plurality of columns 3 each comprising at least one adsorbent phase. Each column or adsorbent cartridge, which permits fixing and then eluting and concentrating the organic compounds, is comprised generally of a tube of a diameter of 6.35 mm constituted by an inert material which can be glass, "Teflon" (trademark) or a high density plastic. In the example described below, the body of the columns used is of high density polyethylene. This tube terminates in two fittings permitting sealed connection to the rest of the installation. The connection is designed to resist a pressure of several bars.

The phase used is dependent on the application. In the example described hereafter, the phase used is a polymeric compound. This phase is maintained in the tube by two stainless steel sintered members. The phase volume is of the order of several milliliters. In the example given below, it is 0.5 ml. The sintered pieces used have a cutoff threshold of several microns. To avoid any untimely plugging, it is thus necessary to use specimens that have been pre-filtered to 10 µm.

In a manner characteristic of the invention, the extraction device comprises, on both sides of the columns 3, a valve 4 controllable to switch from one column 3 to another to place in action a column 3 adapted to ensure the extraction function when another column 3 is in a non-working condition. The switching of each switching valve 4 permitting the placing in operation of one column 3 adapted to ensure the extraction function when the other column is in a non-working condition, is controlled by means of a plugging up detection device for the columns 3 so as to ensure automatic operation of the extraction device. Thus, in this case, when one column is plugged, the installation automatically switches to a new column 3.

The device for detecting the plugged condition of the columns can be constituted by a device 6 for measuring pressure, such as a pressure detector with a flush membrane. This pressure measuring device 6 can be positioned between the low pressure pump 2 for supplying the extraction device, and a valve 5, which will be described hereafter, said direction inverting valve. The use of a pressure detector 6 with a flush membrane permits avoiding dead spaces. The switching pressure can be programmed according to the use.

In the illustrated examples, the switching valves 4 that are used are multi-path slide valve also called a valve with n paths and n−1 positions. Such valves are particularly produced by the Rheodyne: Labpro company. They are of the 7 path, 6 position low pressure type, with a $\frac{1}{16}^{th}$ inch connector and are referred to as Touzart and Matignon 014.439.10. Another valve produced by Valco, Cheminert C25Z, with 6 to 10 paths, $\frac{1}{16}^{th}$ inch connector, called Touzart and Matignon 136.011.30, 136.011.31, 136.011.32 could also be used.

These valves comprise, like the valve 1 of the distribution device, N peripheral paths connected to a column 3 and a central common path adapted to be connected selectively with one peripheral path. This central path is moreover connected to a direction reversing valve 5 which will be described hereafter.

The presence alone of the switching valves would not suffice to permit the installation to operate in an autonomous manner over fairly long periods of time. As a result, further to increase the period of operation of such an installation, it is necessary to increase the lifetime of each column. To do this, a direction reversing valve 5 is interposed between each switching valve 4 and the low pressure pump 2. This direction reversing valve 5 is thus common to each switching valve 4. This controllable direction reversing valve 5 is arranged to impress one direction of circulation of the fluid in any one of the columns 3 of the switched extraction device by the switching valves 4 and to ensure the return of this fluid to the valve 5 so as then to distribute the treated fluid toward a circuit that is selected either to put it away or to analyze it. This direction reversing valve 5 can be constituted by a valve with n paths and 2 positions, such as a low pressure Rheodyne: Labpro valve, 6 paths, 2 positions, $\frac{1}{16}^{th}$ inch connector, referred to as Touzart and Matignon 014.439.12 or a Valco valve, Cheminert C22Z, 6 to 10 paths, $\frac{1}{16}^{th}$ inch connector, calleld Touzart and Matignon 136.011.16, 136.011.17, 136.011.18.

The control means for the direction reversing valve 5 are subject in operation to a cycle of operations pre-programmed as a function of the preparation of the specimen to be carried out. Thus, as shown in the figures, as a function of the position of the valve 5, the circulation of the fluid will take place in a first circulation direction within the column 3 or according to a second circulation direction called countercurrent, within the column.

The installation further comprises, downstream of the direction reversing valve 5 and connected to this latter, a valve 7 called a controllable selection valve to deliver the treated fluid either toward an analysis device 8, not shown in detail, or toward an installation 9 for rejection or discard (not shown). Contrary to the switching valves 4, whose control is a function of signals supplied by the detection device 6, the control means for the direction reversing valve 5 and the selection valve 7 are subject in operation to a cycle of operations pre-programmed as a function of the preparation of the specimens to be carried out. However, the switching of the switching valves 4 cannot take place during the analysis of a specimen. This switching can take place only after the different analysis cycles have been carried out.

For the control, the installation includes a computer provided with software permitting configuring as desired the extraction/concentration process. The software is designed to permit free programming of each element of the system such that the operator can completely program his methods of concentration. The control automation of the system regulates a series of sequences of pumping which define a concentration method. One pumping sequence is defined by a succession of switching orders for the different valves and terminates with the end of the pumping action, which is to say the programming of the volume to be pumped and of the speed or time of pumping. These different sequences are coded into a control panel according to a simple control language which is then interpreted by the control software. One method of concentration corresponds to one file. This control software also is responsible for the control of the switching of the columns of the extraction device. It acquires the measurement of internal pressure of the circuit of the installation and, as a function of an adjustable threshold, decides on the switching to a new column. This software displays the condition of the different columns. It positions an indication when the last column is switched. The frequency of measurements is programmable in real time and can be controlled by an external computer.

Of course, all of the elements of the installation described above are constituted by inert material resistant to corrosive liquids without thereby releasing traces of organic compounds adapted to interfere with the ultimate analysis. The materials that can be used are particularly stainless steel, ceramics and Teflon. The hydraulic connections between the different elements are ensured by Teflon tubes.

Thanks to such an installation, it is possible to use processes in which, after loading the specimen into the column 3, such as natural or treated waters eventually adapted for consumption, adapted to contain pesticides or other organic pollutants, said column 3 is successively subjected to a cycle of rinsing, a cycle of elution, then a cycle of regeneration, the loading cycle and the rinsing cycle being operated according to a first direction of circulation of the fluid in the column whilst the elution cycle and regeneration cycle are carried out by countercurrent circulation of fluid in the column. The circulation of the fluid in the course of these cycles is shown by a wider line in FIGS. 1 to 4 which correspond respectively to the cycle of regeneration, the cycle of loading, the cycle of rinsing and the cycle of elution.

Moreover, the circuit of the installation is subjected between each cycle to the actions of purging and reconditioning each dead volume, in particular between valves.

Parallel to these cycles, there is detected in real time and continuously the state of wear of the column 3, ensuring the function of extraction, and there is actuated, by means of the switching valves 4, another column 3 adapted to ensure the extraction operation when the active column 3 is detected as being in a non-working condition.

Thus, by way of example, an operating protocol is given hereafter. A first volume of 5 ml of methanol is placed in the column to condition it. Then 5 ml of distilled water are placed to eliminate any trace of solvent after concentration. These two steps (FIG. 1) are carried out in the reverse direction of loading and at a speed of 5 ml/mn. The water load (FIG. 2), corresponding to the specimen to be prepared, is carried out at 10 ml/mn. Rinsing of the column (FIG. 3) is carried out at 5 ml/mn in the loading direction with distilled water, comprising a certain percentage of acetonitrile. This percentage can vary as a function of the compounds that are sought. Additions of acid or salt can be carried out in the case of poor retention of the compounds. Elution of the column (FIG. 4) takes place in the reverse direction of loading at a speed of 1 ml/mn. The system is so calibrated as to retain only 1 ml of the most concentrated eluate. The regeneration of the column takes place at the same time as the step of conditioning the column with methanol.

It is to be noted that the low pressure volumetric pump does not operate during switching of the valves 4, 5, 7. The reprogrammable file for each specimen preparation to be carried out contains therefore all the information necessary for practicing such a protocol. It moreover comprises information on the positions that are to be taken by the valves for each cycle.

The final analysis can be carried out by UV or visible spectrophotometry or by any other method of detection or separation for a liquid effluent, such as for example refractometry, fluorescence, electrochemistry, conductivity, radioactivity, mass spectrometry, high performance liquid chromatography or the like. In the case of an installation measuring UV, there is preferably used a visible UV spectrophotometer with sweeping or with a bar of diodes provided with a multi-well system permitting the analysis of several measurement paths provided with wells of a diameter and an optical path of different sizes so as to be able to analyze raw waters that are loaded and an eluate of low volume. So as to decrease the instrument noise, several consecutive acquisitions of spectra will be carried out, the spectra being then averaged.

The analysis of the UV spectrum can be based on the deconvolution method proposed by Professor Thomas of the School of Mines of Ales. This method is integrated into the Secoman spectrophotometer in a standard method. The columns 3 of the mentioned installation can be used a large number of times. Tests that have been carried out give a number of uses of the order of 80 before overpressures appears which indicate plugging of the column. The extraction output is very high. It is independent of aging of the column.

The invention claimed is:

1. Installation for the automatic preparation of specimens, particularly of concentrates of organic compounds dissolved in a liquid phase, for line analysis in a suitable measuring system such as a UV spectrometer, an infrared device, a fluorimeter, a mass spectrometer or the like, this installation comprising
    a) a device for receiving a liquid specimen,
    b) a distribution device comprising a valve (1) capable of selecting either the specimen, or one of the different solvents or reagents needed for a liquid/solid extraction process,
    c) a low pressure pump (2) receiving the output of the distribution device and permitting supplying at the selected flow rate a liquid/solid extraction device,
    d) a liquid/solid extraction device comprising several columns (3) each comprising at least one adsorbent phase,
    the extraction device comprising, on opposite sides of the columns (3), a valve (4) controllable to switch one column (3) to another to place in action a column (3) adapted to ensure the extraction operation when another column (3) is in a non-working condition, each switching valve (4) being connected to a common direction reversing valve (5) interposed between the pump (2) and the switching valves (4), this controllable direction reversing valve (5) being disposed downstream of said pump (2) and upstream of both of said switching valves (4) being arranged to impose as a function of the position of the controllable direction reversing valve (5) a direction of circulation of fluid that has not passed through any of said columns (3), in a first circulation direction within any one of the columns (3) of the extraction device or of fluid that has not passed through any of said columns (3), in a second countercurrent direction within any one of the columns (3) of the extraction device and to ensure its return to said valve (5) to distribute the treated fluid toward a selective circuit either for discard, or for analysis.

2. Installation according to claim 1, characterized in that the switching of each switching valve (4) permitting the operation of a column (3) adapted to ensure the extraction operation when another column is in a non-working condition, is controlled at least by means of a device for detecting plugging of the columns (3) so as to ensure automated operation of the extraction device.

3. Installation according to claim 2, characterized in that the device for detecting the condition of plugging of the columns is a pressure measuring device (6) preferably a flush membrane pressure detector.

4. Installation according to claim 3, characterized in that the pressure measuring device (6) is disposed between the low pressure pump (2) for supplying the extraction device and the direction reversing valve (5).

5. Installation according to claim 1, characterized in that it comprises, downstream of the direction reversing valve (5) and connected to this latter, a so-called controllable selection valve (7) to deliver the treated fluid either toward an analysis device (8) or toward a rejection installation (9).

6. Installation according to claim 5, characterized in that the control means of the direction reversing valve (5) are subject in operation to a cycle of operations preprogrammed as a function of the preparation of the specimen to be carried out.

7. Installation according to claim 1, characterized in that the switching valve (4) is a multi-path slide valve.

8. Installation for the automatic preparation of specimens, particularly of concentrates of organic compounds dissolved in a liquid phase, for line analysis in a suitable measuring system such as a UV spectrometer, an infrared device, a fluorimeter, a mass spectrometer or the like, this installation comprising
   a) a device for receiving a liquid specimen,
   b) a distribution device comprising a valve (1) capable of selecting either the specimen, or one of the different solvents or reagents needed for a liquid/solid extraction process,
   c) a low pressure pump (2) receiving the output of the distribution device and permitting supplying at the selected flow rate a liquid/solid extraction device,
   d) a liquid/solid extraction device comprising several columns (3) each comprising at least one adsorbent phase,
   the extraction device comprising, on opposite sides of the columns (3), a valve (4) controllable to switch one column (3) to another to place in action a column (3) adapted to ensure the extraction operation when another column (3) is in a non-working condition, each switching valve (4) being connected to a common direction reversing valve (5) interposed between the pump (2) and the switching valves (4), this controllable direction reversing valve (5) being disposed downstream of said pump (2) and upstream of both of said switching valves (4) having at least two positions, one position in which the controllable direction reversing valve (5) is arranged to impose a direction of circulation of the fluid that has not passed through any of said columns (3), via one of the switching valves (4) said first switching valve in a first circulation direction within any one of the columns (3) of the extraction device and to ensure its return via the other of the switching means (4) said second switching valve to said controllable direction reversing valve (5) to distribute the treated fluid toward a selective circuit either for discard, or for analysis and another position in which the controllable direction reversing valve (5) is arranged to impose a direction of circulation of fluid that has not passed through any of said columns (3), via the other of the switching means (4) said second switching means, in a second countercurrent direction within any one of the columns (3) of the extraction device and to ensure the return of the fluid via the other of the switching means (4) said first switching means to said valve (5) to distribute the treated fluid toward a selective circuit either for discard, or for analysis.

9. Installation according to claim 8, characterized in that the switching of each switching valve (4) permitting the operation of a column (3) adapted to ensure the extraction operation when another column is in a non-working condition, is controlled at least by means of a device for detecting plugging of the columns (3) so as to ensure automated operation of the extraction device.

10. Installation according to claim 9, characterized in that the device for detecting the condition of plugging of the columns is a pressure measuring device (6) preferably a flush membrane pressure detector.

11. Installation according to claim 10, characterized in that the pressure measuring device (6) is disposed between the low pressure pump (2) for supplying the extraction device and the direction reversing valve (5).

12. Installation according to claim 8, characterized in that it comprises, downstream of the direction reversing valve (5) and connected to this latter, a so-called controllable selection valve (7) to deliver the treated fluid either toward an analysis device (8) or toward a rejection installation (9).

13. Installation according to claim 12, characterized in that the control means of the direction reversing valve (5) are subject in operation to a cycle of operations preprogrammed as a function of the preparation of the specimen to be carried out.

14. Installation according to claim 8, characterized in that the switching valve (4) is a multi-path slide valve.

* * * * *